(12) United States Patent
Godefroy et al.

(10) Patent No.: US 8,603,773 B2
(45) Date of Patent: Dec. 10, 2013

(54) METHOD AND SYSTEM FOR ANALYZING A BLOOD SAMPLE

(75) Inventors: Christophe P. Godefroy, Miramar, FL (US); John Steven Riley, Miami, FL (US); Patricio J. Vidal, Miami, FL (US)

(73) Assignee: Beckman Coulter, Brea, CA (US)

( * ) Notice: Subject to any disclaimer, the term of this patent is extended or adjusted under 35 U.S.C. 154(b) by 715 days.

(21) Appl. No.: 12/730,977

(22) Filed: Mar. 24, 2010

(65) Prior Publication Data
US 2010/0240055 A1  Sep. 23, 2010

Related U.S. Application Data

(63) Continuation-in-part of application No. 12/234,275, filed on Sep. 19, 2008.

(51) Int. Cl.
*C12Q 1/06* (2006.01)
*G01N 33/49* (2006.01)
*G01N 21/00* (2006.01)
*G01N 1/38* (2006.01)

(52) U.S. Cl.
USPC ............... 435/39; 436/63; 436/172; 436/175

(58) Field of Classification Search
None
See application file for complete search history.

(56) References Cited

U.S. PATENT DOCUMENTS

| | | | |
|---|---|---|---|
| 5,616,501 A | 4/1997 | Rodriguez et al. | |
| 6,060,322 A | 5/2000 | Horton et al. | |
| 6,410,330 B1 | 6/2002 | Li et al. | |
| 6,472,215 B1 | 10/2002 | Huo et al. | |
| 2004/0132196 A1 | 7/2004 | Mizukami et al. | |
| 2006/0160229 A1 | 7/2006 | Lopez et al. | |
| 2007/0105230 A1 | 5/2007 | Perez et al. | |
| 2009/0076736 A1 | 3/2009 | Ikeuchi et al. | |

OTHER PUBLICATIONS

Poon, C.Y. In Remington: The Science and Practice of Pharmacy 21st Ed., Chapter 32. Hendrickson, R. et al., Eds.; Lippincott Williams & Wilkins: New York, 2005; pp. 565-598.*
Mach-Pascual, S., Darbellay, R., Pilotto, P-A., Beris, P. (1996) Eur. J. Haematol., vol. 57, pp. 54-61.*
Beckman Coulter®, "Coluter® 3-D VCS Technology," available online at http://www.beckmancoulter.com/products/instrument/hematology/VCS_Technology.pdf, (accessed Jun. 2008).
Beckman Coulter®, "Advancements in Technology: NRBC Enumeration. UniCel® DxH 800 Coulter® Cellular Analysis System," Beckman Coulter, Inc., Diag-Printed in United States (2009).
Beckman Coulter®, "Advancements in Technology: Reticulocyte Methodology. UniCel® DxH 800 Coulter® Cellular Analysis System," Beckman Coulter, Inc., Diag-Printed in United States (2009).
Kessler, C., et al., "Immature Reticulocyte Fraction and Reticulocyte Maturity Index," available online at http://www.beckmancoulter.com/literature/ClinDiag/recticliterature.pdf, (accessed Jun. 2008).
Prahl, S., "Optical Absorption of Hemoglobin," available online at http://omlc.ogi.edu/spectra/hemoglobin/index.html, (© SAP Dec. 15, 1999; Mar. 4, 1998; and Jun. 8, 1998).
International Search Report for International Application No. PCT/US2010/28683, ISA/US, Commissioner for Patents, U.S.A., mailed on May 12, 2010.
The Written Opinion of the International Searching Authority for International Application No. PCT/US2010/28683, ISA/US, Commissioner for Patents, U.S.A., mailed on May 12, 2010.

* cited by examiner

*Primary Examiner* — Allison Ford
*Assistant Examiner* — Michelle F Paguio Frising
(74) *Attorney, Agent, or Firm* — K&L Gates LLP; Louis C. Cullman (57) ABSTRACT

Methods, systems, and computer program products for the analysis of a blood sample are disclosed. One embodiment is a method of detecting and enumerating hard-to-ghost cells in a blood sample. Another embodiments is a method of analyzing reticulocytes in a blood sample. Methods of using blood count parameters are also provided.

11 Claims, 12 Drawing Sheets

METHOD AND SYSTEM FOR ANALYZING A BLOOD SAMPLE

CROSS REFERENCE TO RELATED APPLICATIONS

This application is a continuation-in-part of U.S. application Ser. No. 12/234,275, filed Sep. 19, 2008, which is incorporated herein by reference in its entirety.

BACKGROUND

1. Field of the Invention

This invention relates in general to the methods and systems for analyzing the blood samples using a particle analyzer, and more particularly to determining reticulocytes and hard-to-ghost cells.

2. Background

Each year, millions of Americans are affected by blood diseases. Examples of blood pathologies include various hematological malignancies, such as leukemias and lymphomas, hemoglobinopathies, which encompass a number of anemias of genetic origin, such as thalassemia, Cooley's Disease, and sickle-cell anemia (HbS disease), as well as various clotting and bleeding disorders. Blood abnormality can also be a secondary consequence associated with other conditions, such HIV/AIDS, malignant tumors, and autoimmune disorders. Most of these conditions have significant morbidity and mortality and commonly cause severe pain in the affected patient. Early diagnosis of these disorders is critical so patients who have the disease can receive proper treatment and disease management.

Blood is a specialized bodily fluid that delivers necessary substances, such as nutrients and oxygen, to the body's cells and transports waste products away from those same cells. The predominant cell in blood is the erythrocyte, i.e., red blood cell or red cell. In a peripheral blood smear, erythrocytes derive their reddish color from protein hemoglobin, and usually appear round or oval with a pale-staining center region. Their biconcave morphology increases the cell's surface area and facilitates diffusion of oxygen and carbon dioxide from the cell. A typical erythrocyte has a lifespan of about 120 days.

Erythrocytes develop from nucleated precursor cells in the bone marrow. Immature erythrocytes, i.e., reticulocytes, have organelles that contribute to an increased hemoglobin content and gas-carrying capacity. Reticulocytes can be recognized in peripheral blood smears when a special stain is used to stain their polyribosome or ribonucleic acid (RNA). Under typical conditions, reticulocytes account for about 1-2% of red blood cells in a sample. However, during certain periods of physical need, the reticulocyte count may increase.

Blood tests can be used to determine physiological and biochemical states, such as disease, mineral content, drug effectiveness, and organ function. In confirming or helping to confirm the diagnosis of diseases such as, for example, various forms of anemia or acute internal hemorrhage, the determination of reticulocytes can be of critical importance.

Automated reticulocyte analysis can be done using a particle analyzer such as a flow cytometer or hematology analyzer. Example particle analyzers include, the UniCel® DxH 800 System from Beckman Coulter and XT-2000 from Sysmex Corporation. The preparation of a blood sample for cytometric flow or hematology analysis generally involves taking a whole blood sample and performing one or both the steps of incubating the sample of blood with a vital stain such as New Methylene Blue (NMB) and diluting the blood sample with a hypotonic acid that clears hemoglobin. The staining precipitates RNA within the erythrocytes. Diluting with a hypotonic acid clears hemoglobin, leaving the stained RNA within the cells. The process of removing hemoglobin is commonly referred to as "ghosting." The blood sample, or portion of it, is then subjected to analysis in a flow cell of a particle analyzer. Typically, cells in a sheath fluid pass through a point in the flow cell, one by one, where they are interrogated by one or more beams of light. Several measurements are generated for each passing cell. The interrogation of a single cell is referred to as a cell event. Commonly recorded measurements per cell event include, forward light scatter, axial light loss, and fluorescence. Some particle analyzers also collect a direct current impedance (DC) measurement which is a measure of how much impedance is exerted by a cell. The DC measurement, which is obtained from applying the maximum current such that the cell membrane is not permeated and no current flows through the cell, is also known as Coulter volume or volume.

SUMMARY OF THE INVENTION

The present application is directed towards the analysis of particle analyzer data. In one embodiment, an automated method of enumerating hard-to-ghost cells in a blood cell sample can include: mixing a blood cell sample with a nucleic acid stain and a ghosting reagent to remove hemoglobin from red blood cells, thereby generating a ghosted blood cell sample; passing the ghosted blood cell sample through a cytometric flow cell; analyzing the ghosted blood cell sample in the cytometric flow cell by using two different optical measurements; differentiating hard-to-ghost cells by detecting the two different optical measurements; and enumerating the hard-to-ghost cells.

In another embodiment a method of analyzing a blood sample can include: measuring the blood sample in a flow cell by a detection comprising an axial light loss measurement to generate event data; identifying a hard-to-ghost cell population using the event data, based on the axial light loss measurement; filtering-out the hard-to-ghost cell population from said event data; and analyzing the event data to identify blood cell distribution patterns. Analysis including the reticulocyte analysis can be performed subsequent to filtering out the hard-to-ghost cells.

In some embodiments, a method of analyzing a blood sample can include the steps of enumerating the population of hard-to-ghost cells using the event data generated by axial light loss measurements. An example of an embodiment that is reported can be % hard-to-ghost cells of a total red blood cell population. Said value can be used as a research use only (RUO) parameter, or can be developed into an in vitro diagnostic (IVD) parameter.

In yet another embodiment, an automated method of enumerating hard-to-ghost cells in a blood cell sample can include: mixing a blood cell sample with a nucleic acid-staining fluorescent dye to stain the blood cells containing nucleic acid and a ghosting reagent to remove hemoglobin from red blood cells in the blood cell sample, thereby generating a ghosted blood cell sample; passing the ghosted blood cell sample through a cytometric flow cell; analyzing the ghosted blood cell sample in the cytometric flow cell by using light scatter and fluorescence measurements; differentiating hard-to-ghost cells from the fluorescently stained cells containing nucleic acid and ghosted cells by detecting fluorescence and light scatter measurements; and enumerating the hard-to-ghost cells.

Further features and advantages of the present invention, as well as the structure and operation of various embodiments thereof, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

FIG. 7 (A) shows a two-dimensional view of DC plotted against UMALS illustrating event data with the capability to identify the hard-to-ghost cell population.

FIG. 7 (B) shows a two-dimensional view of ALL plotted against UMALS illustrating event data with the capability to identify the hard-to-ghost cell population.

FIG. 7 (C) shows another two-dimensional view of DC plotted against UMALS illustrating event data with the capability to identify the hard-to-ghost cell population.

The features and advantages of the present invention will become more apparent from the detailed description set forth below when taken in conjunction with the drawings. In the drawings, like reference numbers generally indicate identical, functionally similar, and/or structurally similar elements. Generally, the drawing in which an element first appears is indicated by the leftmost digit(s) in the corresponding reference number.

DETAILED DESCRIPTION

The present invention relates to particle analysis data processing. While the present invention is described herein with reference to illustrative embodiments for particular applications, it should be understood that the invention is not limited thereto. Those skilled in the art with access to the teachings herein will recognize additional modifications, applications, and embodiments within the scope thereof and additional fields in which the invention would be of significant utility.

Overview

As described in the background section above, the automated ability to determine the distribution of red blood cells in a blood sample is a vital capability for several applications. The methods and systems disclosed herein yield an improved automated measure of cell populations in a blood sample. In one embodiment, the hard-to-ghost cells are differentiated and enumerated using methods provided herein.

Exemplary environments in which this invention may be practiced include particle analyzers, such as Beckman Coulter's UniCel® DxH 800 System. The UniCel® DxH 800 System, for example, uses the Coulter proprietary Volume, Conductivity, and LightScatter (VCS) technology to evaluate hydrodynamically focused cells within a flow cell. VCS uses three independent energy sources that work in concert with each other for cell measurement: a low frequency direct current power source to measure volume; a high frequency power source to measure conductivity, and a laser light source to measure scatter. The volume measurement is performed using the Coulter principle of electrical impedance to physically measure the volume that the entire cell displaces in an isotonic diluent. This method accurately sizes all cell types regardless of their orientation in the light path. Alternating current in the radio frequency (RF) range short circuits the bipolar lipid layer of a cell's membrane, allowing the energy to penetrate the cell. This powerful method is used to collect information about cell size and internal structure, including chemical composition and nuclear volume. A laser and multiple-angle light scatter detectors provide information about a cell's internal structure, granularity, and surface morphology. In addition, VCS devices use the highly accurate DC measurement of volume to obtain other measurements that are adjusted for cell size from conductivity and scatter. U.S. Pat. No. 5,616,501 (to Rodriguez et. al), U.S. Pat. No. 6,060,322 (to Horton et. al), U.S. Pat. No. 6,410,330 (to Li et. al), and U.S. Pat. No. 6,472,215 (to Huo et. al), all of which are hereby incorporated by reference in their entirety, describe the use of VCS technology with respect to detecting reticulocytes and other reticulated cells. It should be noted, however, that the teachings in this disclosure are not limited to devices using VCS technology.

Figure 1:
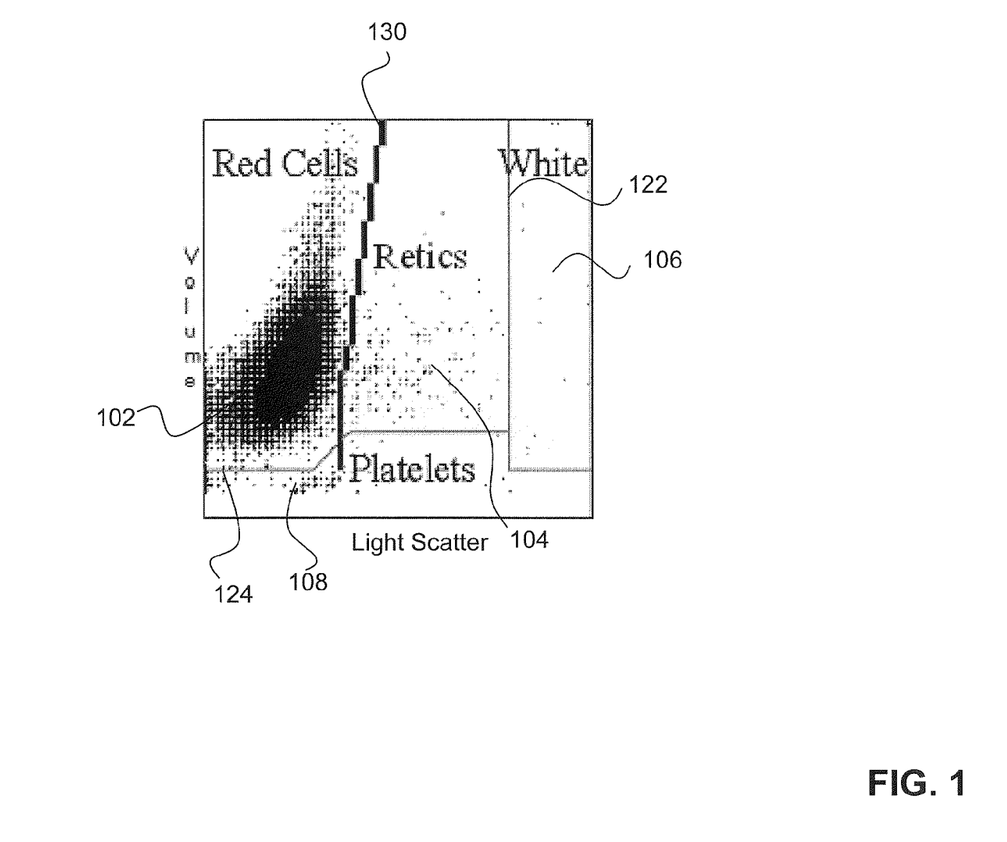
FIG. 1 is a view of event data from analysis of a blood sample using a flow cytometer, in two-dimensions.

FIG. 1 shows a two-dimensional scatter plot of a blood sample based on event data generated from measurements of blood using a particle analyzer. Each data point appearing in the scatter plot is based on selected measurements obtained from one cell event, i.e., the interrogation of an individual cell by an electric current and a laser beam in the flow cell. Event data populations of different cell types commonly found in a blood sample are shown in the scatter plot. In general, sufficient separation exists between the populations of red cells as a whole (i.e., erythrocytes 102 and reticulocytes 104), platelets 108, and white cells 106, that known techniques allow for gating the red cell population as a whole, for example, based on the area defined by lines 122 and 124. Gating refers to the process of filtering selected measurements from multi-parameter data, for example, as described above, separating red cells (erythrocytes and reticulocytes), platelets and white blood cells by testing the measurements generated for each cell event against known threshold values. For example, line 124 can be a threshold volume value and line 122 can be a threshold light scatter value, where cell events with volume measurements above line 124 and light scatter (often used in the form of log of light scatter) value less than line 122 correspond to either erythrocytes or reticulocytes. In existing systems, the reticulocyte population can also be gated, for example, by a line such as line 130. The events to the right of line 130 are reticulocytes, whereas the events to the left of line 130 are mature red cells.

Analyzing Reticulocytes

Figure 2:
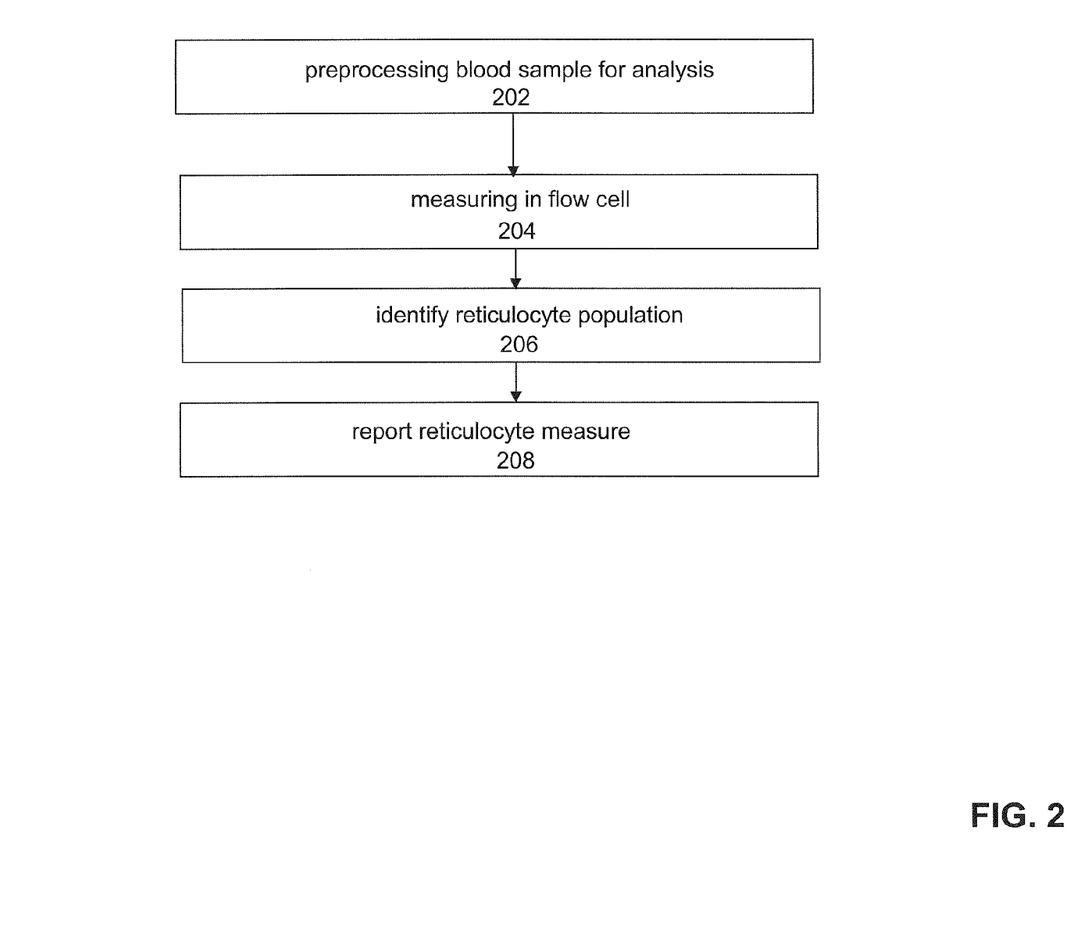
FIG. 2 illustrates steps in analyzing immature reticulocytes in a blood sample according to an embodiment of the present invention.
Figure 3:
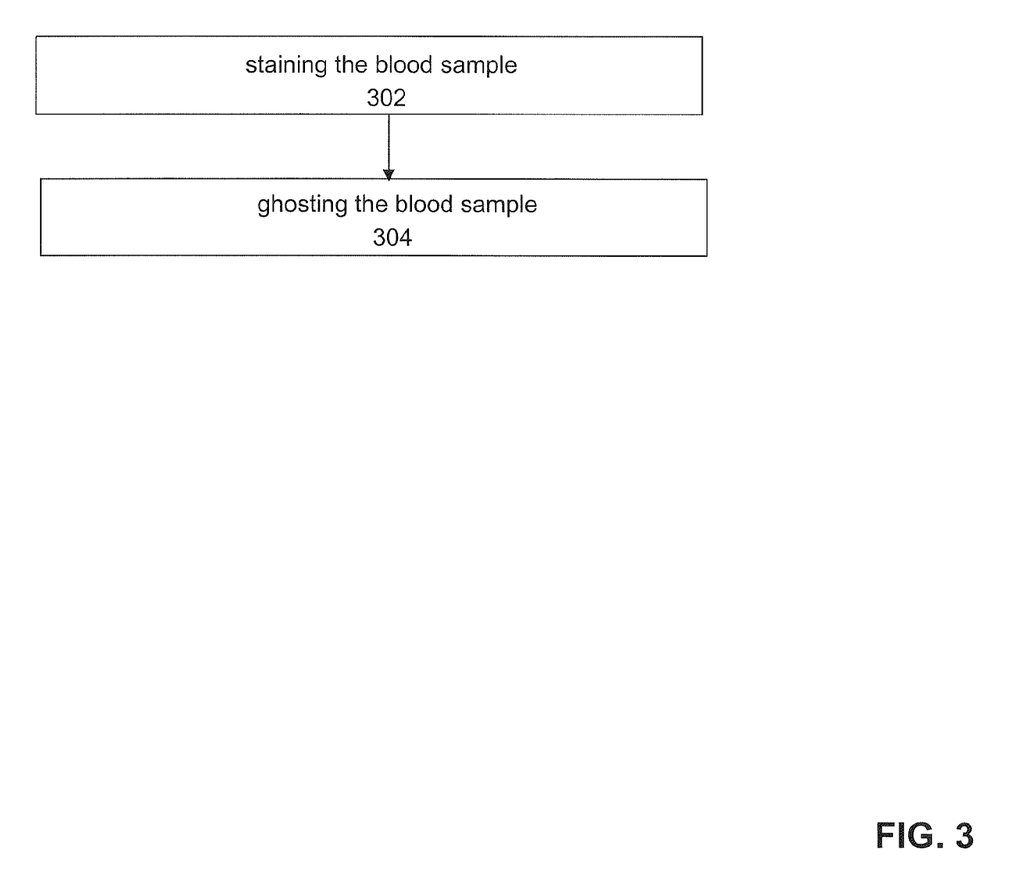
FIG. 3 shows further details of the preprocessing step shown in FIG. 2, according to an embodiment of the present invention.

In one aspect, methods for analyzing reticulocytes in a blood sample are presented. FIG. 2 is a flowchart of steps in evaluating reticulocytes according to an embodiment of the present invention. In step 202, a blood sample is prepared for analysis in a particle analyzer. Preparation can include ghosting the blood sample and/or staining the sample with a suitable dye or stain. FIG. 3 illustrates preparation step 202 in further detail, according to one embodiment. In step 302, the blood sample can be combined with a vital stain to further delineate reticulocytes. For example, a non-fluorochrome dye that precipitates intracellular ribonucleic acid (RNA) of the reticulocyte can be used. Examples of suitable stains include, but are not limited to, New Methylene Blue (known as Reagent A of the Coulter Retic Pak™), Oxazine 750, and Brilliant Cresyl Blue. RNA, having been precipitated, will have higher density which will enhance the delineation of the RNA content in each cell. Using a non-fluorescent dye to measure reticulocytes has the added advantage to allow the blood sample to be further analyzed for other constituents by utilizing a fluorescent dye, if desired. Examples of suitable fluorescent dyes include, but are not limited to, thiazole orange and polymethine. Additional preparatory steps are possible in various embodiments of the present invention. For example, in some embodiments a fluorescent dye can be combined with the blood sample to measure additional properties of the sample using a fluorescence measure.

To further effectuate the examination of a composition of a blood sample, the blood sample can be combined with a reagent such as, for example, a reticulocyte ghosting solution having potassium thiocyanate and sulfuric acid (step 304). This type of ghosting reagent can be obtained as a commercial product known as Reagent B of the Coulter Retic Pak™. Other ghosting reagents known to those skilled in the art can be used. The ghosting process releases the hemoglobin in red blood cells, resulting in ghosted cell. The term "ghosted cell", as used herein, refers to a red blood cell that has more that about 70% of its hemoglobin content removed. Preferably, the cell has more than 90% and even more preferred has more than 95% of the hemoglobin removed. In other words, the ghosted cell retains less than 30% of its original hemoglobin. The reduction of the hemoglobin content enhances the definition of the reticulum to permit cytometric flow determination of the reticulocytes. More specifically, the reduction in hemoglobin content of the red blood cells enables the differentiation of the reticulocytes from the mature RBC when measuring by a non-fluorescent method comprising light scatter and DC.

In addition to facilitating the release of hemoglobin, the ghosting process can also sphere the red blood cells giving the cells a more regular shape, and thereby permitting more predictable light scatter measurements. The native reticulocyte has an irregular shape which produces unpredictable light scatter information when subjected to a light beam. The sphering of the red blood cell provides reproducible light scatter information which forms the basis for determining the reticulocytes in the sample. In some embodiments, it might be advantageous to combine the blood sample with a sphering agent. The sphering agent is used in an amount effective to cause the reticulated erythrocytes and red blood cells to isovolumetrically sphere to eliminate orientation artifacts in analysis of the reticulocytes. In some embodiments, the sphering reagent is a zwitterionic surfactant which isovolumetrically spheres the red blood cells. Examples of sphering agents suitable for the present invention include, but are not limited to, lauroamidopropylbetaine, cocoamidopropylbetaine and cocoamidosulfobetaine.

It has been previously found that the ghosting process is affected by temperature. See, e.g., U.S. Pat. No. 5,616,501, incorporated by reference herein. Temperatures below 55° F. appear to retard the ghosting process and longer time periods are necessary to permit the ghosting process to occur. In some embodiments, the blood sample will be mixed with the ghosting solution at a temperature of at least 55° for approximately 30 seconds. In one embodiment, ghosting of blood sample will be conducted at 106° F. (41° C.).

In some embodiments, the pH of the ghosting solution should be not higher than 3.0. In one embodiment, the pH of the ghosting solution is approximately 1.0 to 2.0. In addition, it appears that the acidic ghosting solution solubilizes the hemoglobin and facilitates its removal from the blood cell. It has been noted that when utilizing potassium thiocyanate, sulfuric acid is the preferred acid to be utilized in the combination. The preferred concentration for the potassium thiocyanate is approximately from 1.0 to 6.0 grams per liter, and for the sulfuric acid is approximately from 0.7 to 3.0 grams per liter.

The osmotic pressure of the ghosting solution should be controlled so that there is a rapid, but controlled swelling of the blood cell. The osmotic pressure of the ghosting solution should be at least about 75 milliosmoles. The osmotic pressure causes the blood cell to swell and release the hemoglobin within thirty (30) seconds of mixing with the ghosting solution. If the osmotic pressure is less than about 75 milliosmoles, then the blood cell will not retain an intact cell membrane and will lyse. More specifically, lower osmotic pressure results in red cells that are damaged so that reticulocyte enumeration is not reliable. If the osmotic pressure is not sufficient, the blood cells will retain hemoglobin which will obscure reticulocyte differentiation. In some embodiments, the osmotic pressure of the ghosting solution will range from about 75 to about 110 milliosmoles. In other embodiments, the osmotic pressure of the ghosting solution will be in the range of about 82 to about 105 milliosmoles.

Figure 4:
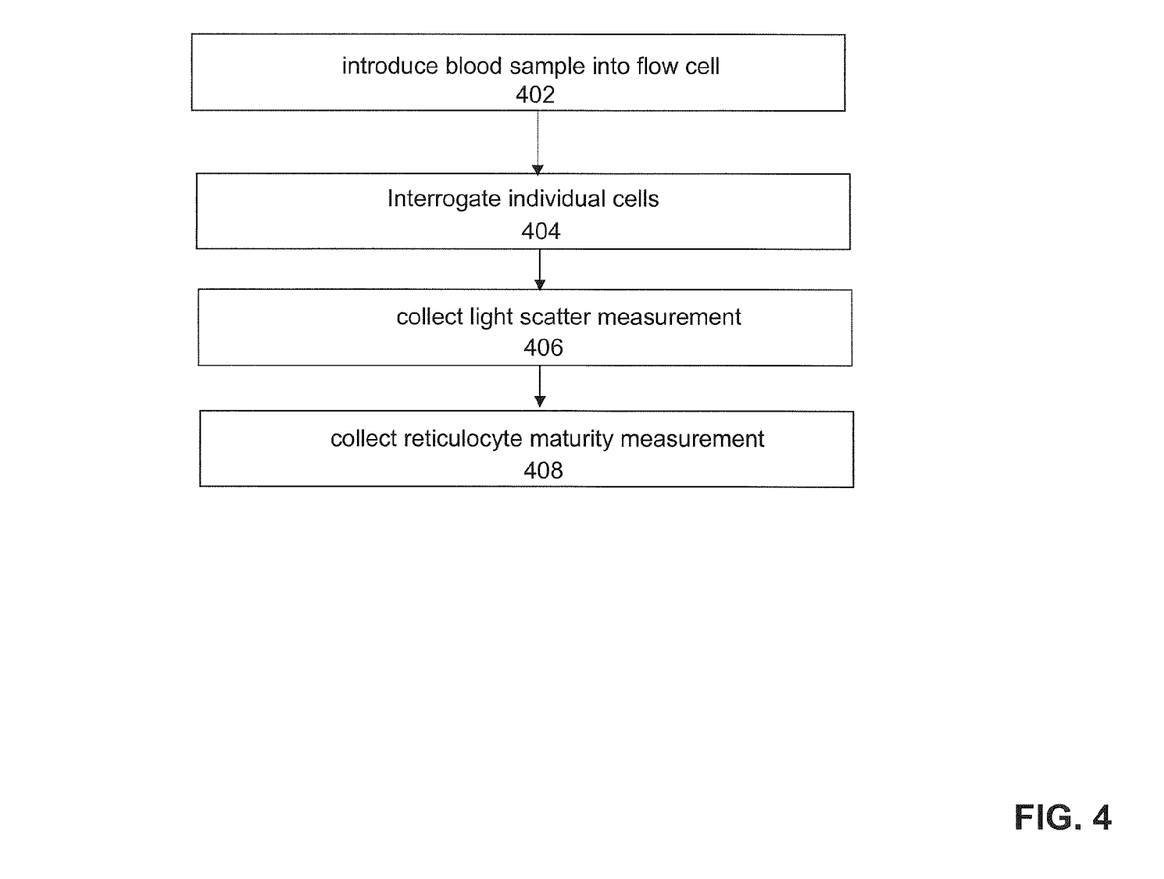
FIG. 4 shows further details of the measuring step shown in FIG. 2, according to an embodiment of the present invention.

Returning to FIG. 2, in step 204, the blood sample is analyzed using a particle analyzer. In one embodiment, the particle analyzer is a hematology analyzer. For example, the blood sample, or a portion of it, is introduced into the particle analyzer. Under hydrodynamic pressure, the blood sample flows, cell by cell, through a flow cell. Within the flow cell, several parameters of the individual cells are measured. For example, particle analyzers using the VCS technology can perform the volumetric sizing of a cell, conductivity of a cell, and light scatter, simultaneously for each cell. FIG. 4 is a flowchart of step 204 in further detail, according to an embodiment of the present invention.

In step 402, the blood sample prepared in step 202, is introduced into a flow cell for analysis. In step 404, in one embodiment, the sample is interrogated by energy from three independent sources as it flows, cell by cell, through an interrogation point in the flow cell. In step 406, the light scatter measurement is recorded for each cell event. As the RNA content decreases with the maturity of the reticulocyte, it can be expected that the light scatter measurement decreases. Several measurements of light scatter can be available, for example, and without limitation, include forward light scatter measurements. Forward scatter measures the light that passes through the cell being interrogated and that is deflected from the axis of the beam of light. Examples of forward light scatter include, but are not limited to, lower median angle light scatter (LMALS), upper median angle light scatter (UMALS), and low angle light scatter (LALS). The LMALS refers to light scattered at an 9°-19° angle from the axis of the beam, UMALS refers to light scattered at an 20°-43° angle from the axis of the beam, and LALS refers to light scattered at approximately 5.1° angle from the axis of the beam. Another light scatter measurement, side angle light scatter (SALS), can measure light scattered at 90° angle. In some embodiments, the analyses of blood sample will include a measurement of axial light loss (ALL). ALL is the amount of light lost at about 0° to 0.5° angle relative to the axis of the beam.

In step 408, another measurement that is indicative of reticulocyte maturity is collected. For example, in one embodiment of the present invention, the size of the cell can be measured. The size of the cell is known to decrease with the maturity of the reticulocyte, in general, as the RNA content decreases. As an example, the size of the cell, or cell volume, can be measured using the DC measurement. The peak amplitude of the DC pulse is a function of cell volume. Other measurements indicative of reticulocyte maturity, including direct or indirect ways of measuring the volume of the cell, can be used in this step. For example, fluorescence measurement to indicate the amount of RNA in the cell, or other modes of measuring cell volume can be used. As another example, forward scatter can also be used to indicate cell size.

Returning to FIG. 2, in step 206 a reticulocyte population is identified from the entire cell event population. Scatter plots of the event data, using various axis, help identify blood cell distribution patterns. As an example, the event data can be visualized in a scatter plot, such as, for example, FIG. 1, where the light scatter is on the x-axis and volume (DC) is on the y-axis. As indicated earlier with respect to FIG. 1, the reticulocyte population 104 can be identified separately from erythrocytes 102, platelets 108 and white cells 106. The accuracy of the reticulocyte population is dependent particularly on how definitively line 130 separating the reticulocytes from the red cells can be determined. For example, in one embodiment, while line 130 can be superimposed on the scatter plot 100 based on threshold light scatter and volume measurement values derived empirically from previous collections of measurements, line 130 can fail to correctly separate erythrocytes 102 from reticulocytes (104), particularly with regard to cell events that lie in close proximity to line 130 in scatter plot 100.

Returning yet again to FIG. 2, in step 208, one or more reticulocyte measures can be reported. In one embodiment the reticulocyte fraction is reported as the ratio of a predetermined number of regions defined on the mapping function to the entire red blood cell population. In another embodiment reticulocytes can be reported as a percentage or absolute number. Reporting involves outputting one or more measurements to a display or other output device such as a computer file.

Detecting Hard-to-Ghost Cells

In one aspect, the method of the present invention allows for the accuracy of reticulocyte detection that is reported to be improved with having more accurate sample data based on which to compute reticulocyte information. It has been observed, in some blood samples, that after the initial ghosting process some cells remain that were either not ghosted or were only partially ghosted, i.e., "hard-to-ghost" cells. For the purposes of the present invention, the term "hard-to-ghost cell" will refer to a cell which has retained at least about more than 30% of its original hemoglobin content. In other words, the hard-to-ghost cell has less than 70% of its original hemoglobin removed. Preferably, the cell has more than 50% and even more preferred has more than 70% of the original hemoglobin content. The ghosting process, for example, by combining a hypotonic acid solution with the blood sample, is intended to clear hemoglobin from the cells. Without ghosting or with inefficient ghosting (i.e., when the cells loose less than about 30% of their hemoglobin content), erythrocytes may not clearly differentiate from reticulocytes. Another view of the difference from ghosted cells compared to hard-to-ghost cells can be seen in FIG. 6 which shows population 610 of the hard-to-ghost cells being positioned in upper portion of the scatter plot of axial light loss versus UMALS. When hard-to-ghost cells are present in the blood sample, and the blood sample is analyzed using light scatter and axial light loss, the differentiation of the reticulocytes from the mature red cells can fail because the hard-to-ghost cell population is dense and is generally positioned within the reticulocyte region. Some embodiments of the present involve detecting hard-to-ghost cells in the total population of blood cells.

Figure 5:
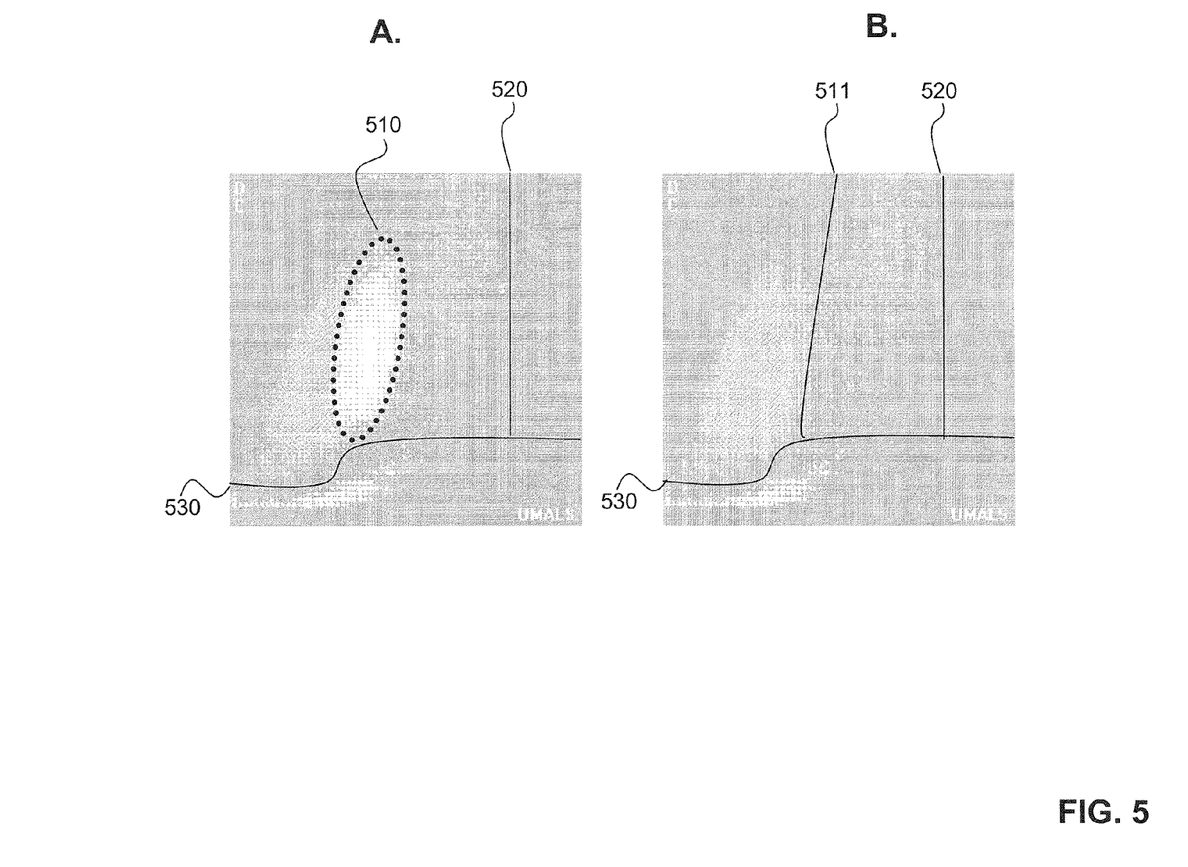
FIG. 5(A) is a two-dimensional view of event data from the analysis of a blood sample.
FIG. 5(B) is a view of the event data shown in FIG. 5(A) with the hard-to-ghost cell population removed.

FIGS. 5(A) and 5(B) show the contrast presented in scatter plots of the same event data with and without hard-to-ghost cell events, using conventional light scatter or upper medium angle light scatter (UMALS), and DC axis. In FIG. 5(A) the scatter plot includes hard-to-ghost cell events. The boundary 510 shows the location of a hard-to-ghost cell event population. FIG. 5(B) shows the same event population after hard-to-ghost cell events, including the population defined by boundary 510, are removed. In both FIGS. 5(A) and 5(B), the events below boundary 530 correspond to platelets and the events to the right of boundary 520 correspond to white blood cells. As can be seen by the location of the boundary 510, the hard-to-ghost cell event population spans the separation of the mature red blood cell population and the reticulocyte population, thereby making it difficult to clearly distinguish between mature red blood cells and reticulocytes. In contrast, when the hard-to-ghost cell event population is removed, as shown in FIG. 5(B), a clear boundary 511 can be defined between the mature red blood cells and reticulocytes. A visual comparison of FIGS. 5(A) and 5(B) illustrates the difficulty in identifying and separating the mature red cells from reticulocytes when hard-to-ghost cells are present.

Figure 6:
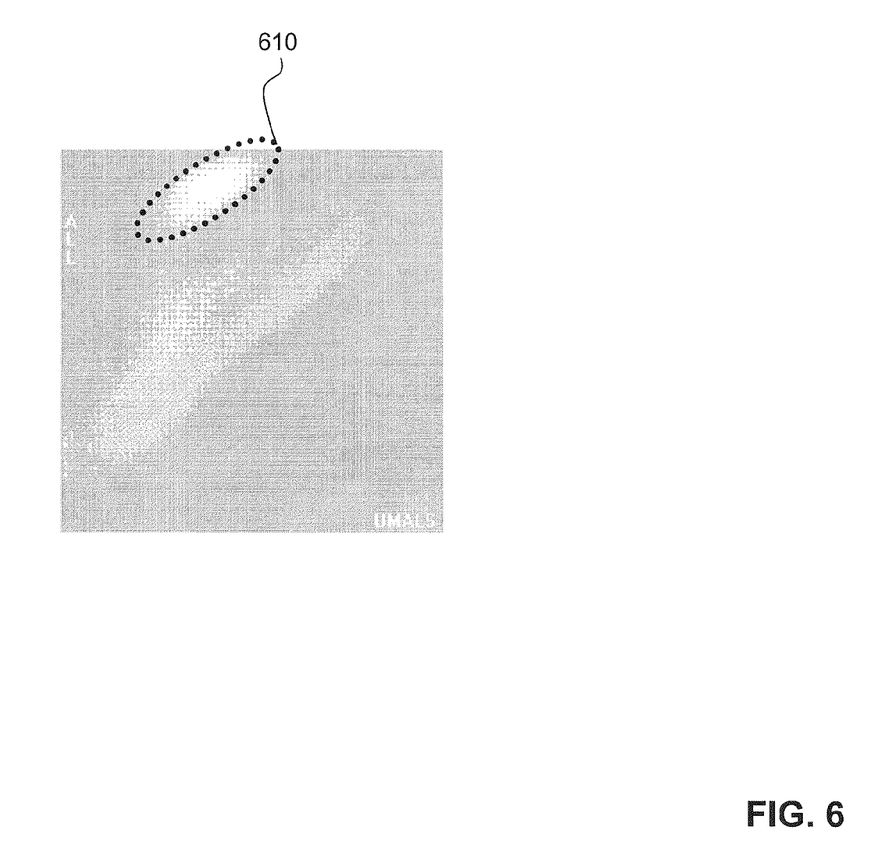
FIG. 6 shows the same event population shown in FIG. 5(A), but using axial light loss (ALL) and UMALS instead of the conventional DC and UMALS.

In this embodiment, the axial light loss measurement enables the discrimination of the hard-to-ghost population from the rest of the sample. It has been unexpectedly found by the inventors of the present invention that the same event population that cannot identify the hard-to-ghost population based on the conventionally used light scatter measurement, can now distinguish the population using an axial light loss measurement. For example, FIG. 6 shows the same event population shown in FIG. 5(A), but using axial light loss (ALL) and UMALS instead of the conventional DC and UMALS. Using ALL, hard-to-ghost cell events can be clearly identified, as shown by the area within the boundary 610.

Figure 7:
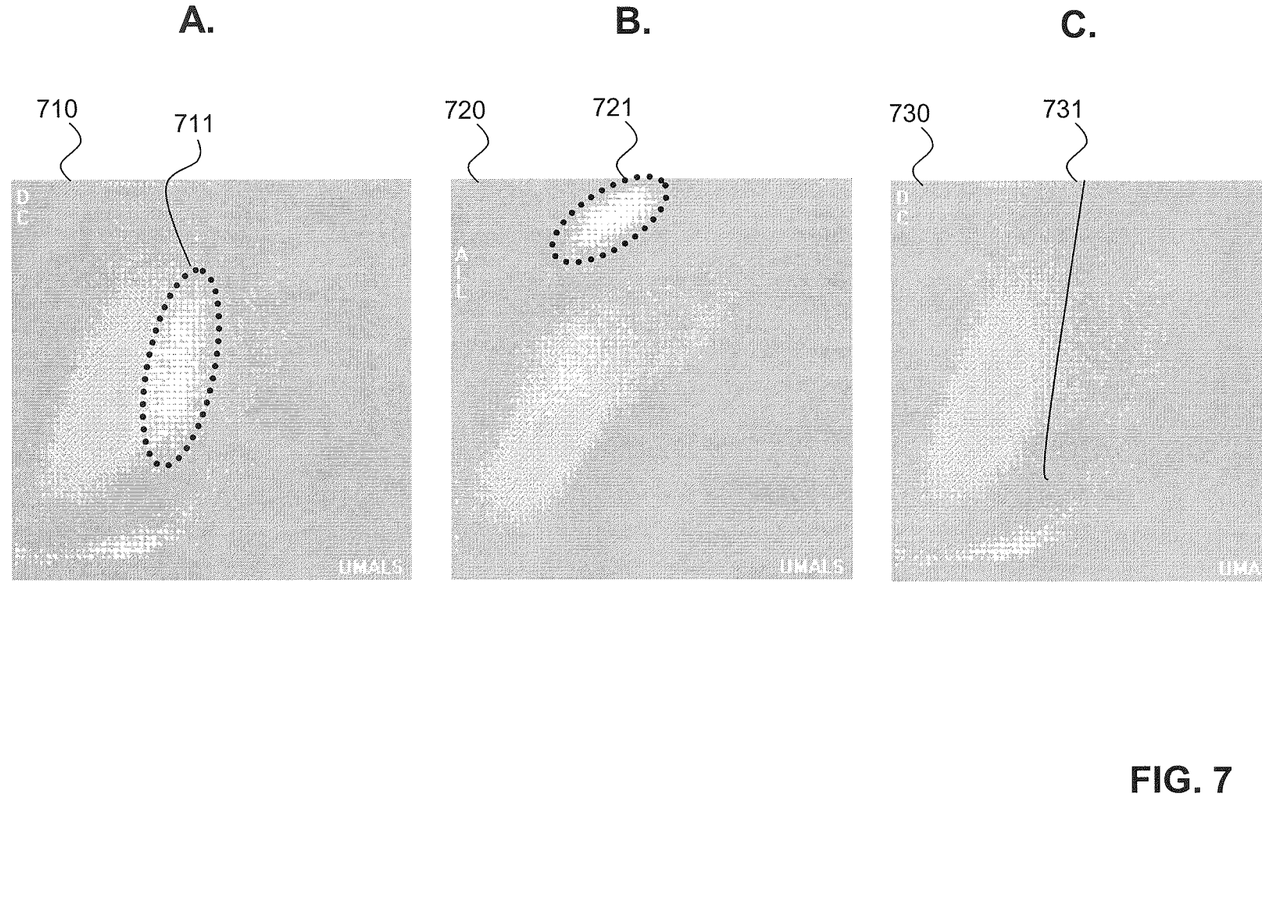

FIGS. 7(A-C) illustrate the hard-to-ghost cell event removal of another blood sample using ALL in an embodiment of the present invention. Scatter plot 710 shows the generally used UMALs and DC. In scatter plot 710, hard-to-ghost cells are present (as shown within boundary 711), but cannot be clearly distinguished from other red blood cells. However, when the same data is shown in scatter plot 720, having axial light loss (ALL) and UMALS as axis, the ability to detect hard-to-ghost cells is vastly improved. Based on ALL, the hard-to-ghost population 721 is clearly discernible from the other event populations.

In one embodiment of the present invention, the cell events corresponding to the hard-to-ghost population can be filtered-out, and the remaining cell events can be displayed in scatter plot, for example such as 730, using UMALS axis and DC axis. Filtering-out cell events corresponding to the hard-to-ghost population can be accomplished by gating the hard-to-ghost population either, automatically based on, for example, threshold ALL and UMALS values determined empirically, or with manual operator assistance. A visual comparison of scatter plots 730 and 710 illustrates the clearer distinction between the mature red blood cell population to the left of boundary 731 and the reticulocyte population to the right of boundary 731.

As shown in FIG. 6 (specifically the area within boundary 610) and FIGS. 7(A-C) (specifically the area within boundary 721), when using ALL, hard-to-ghost cells can be identified as a distinct population from other populations such as mature red blood cells, reticulocytes, platelets and white blood cells. The hard-to-ghost cells generally display a higher ALL than other blood cell types except for white blood cells. White blood cells can be distinguished due to their high light scatter measurements relative to other blood cell types. The high ALL of the hard-to-ghost cell population can be attributed to the relatively high light absorption of hemoglobin. At a laser wavelength of 488 nm (the wavelength used in the particle analyzer that yielded results shown in FIGS. 5(A), 5(B), 6 and 7(A-C)) hemoglobin displays very high optical absorption that leads to a high level of ALL. In general, hemoglobin shows increased absorption of light when the light is between 400-500 nm wavelength.

Figure 8:
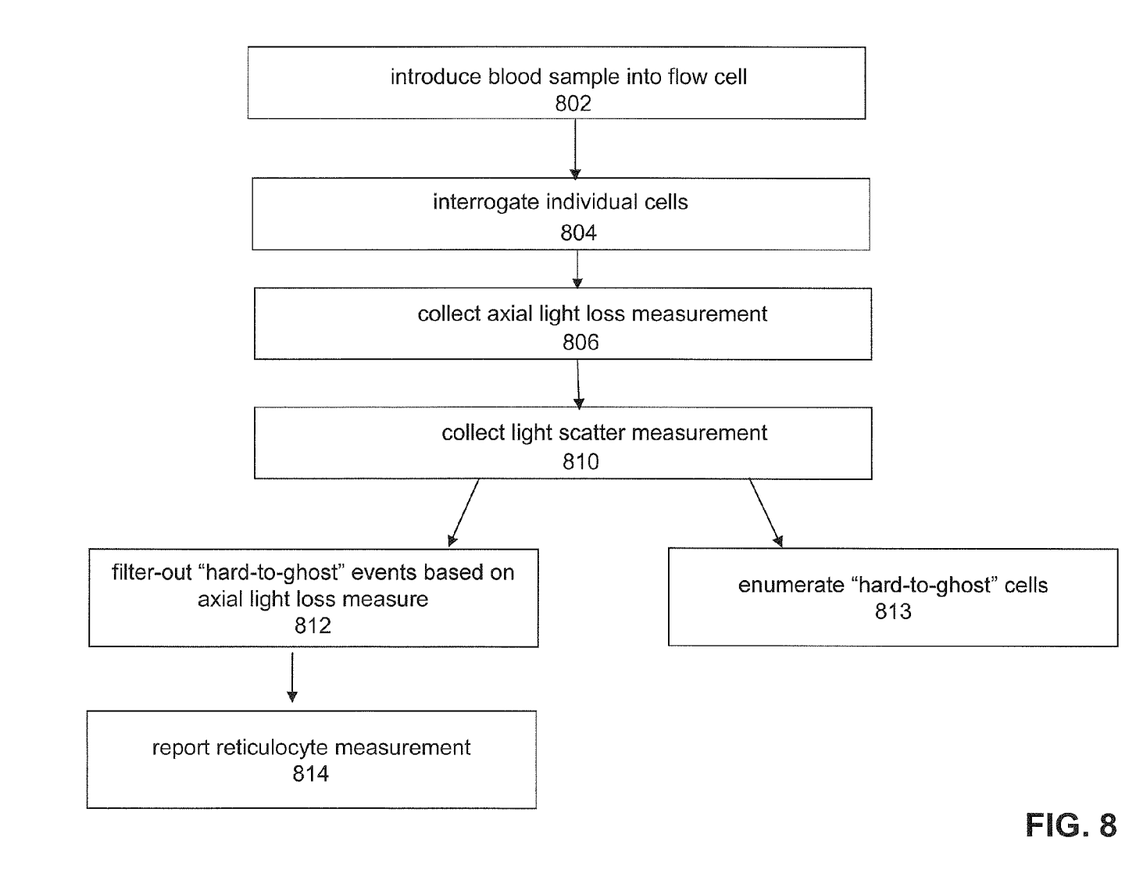
FIG. 8 shows further details of the measuring step shown in FIG. 2, according to another embodiment of the present invention.

Detection of the hard-to-ghost cells in a blood sample being analyzed can be accomplished by the embodiment of the present invention shown in FIG. 8. In FIG. 8, step 202 of FIG. 2 is further dissected to include steps to detect hard-to-ghost cells. In step 802, a prepared blood sample, i.e., a sample having been ghosted and stained, can be introduced to a flow cell for analysis. In step 804, the sample is interrogated, cell by cell, using measurements including a light beam as explained with respect to FIG. 2 above. In step 806, the ALL measurement is collected, along with one or more light scatter measurements in step 810. Descriptions of the light scatter measurement can be found above with respect to FIG. 2.

In one embodiment, once the hard-to-ghost cells are detected, this event data can be used to more accurately analyze reticulocytes. For example, the hard-to-ghost cell population can be filtered out using the ALL values of the reticulocyte events, as in step 812. In this embodiment, the event data will be available for further analysis for determining reticulocyte information or any other red cell information, as in step 814. In general, the removal of the hard-to-ghost cell event population would increase the accuracy of most parameters reported concerning red blood cells and/or reticulocytes. Calculation and reporting of reticulocyte information is described above with respect to FIG. 2.

Enumerating Hard-to-Ghost Cells

Figure 10:
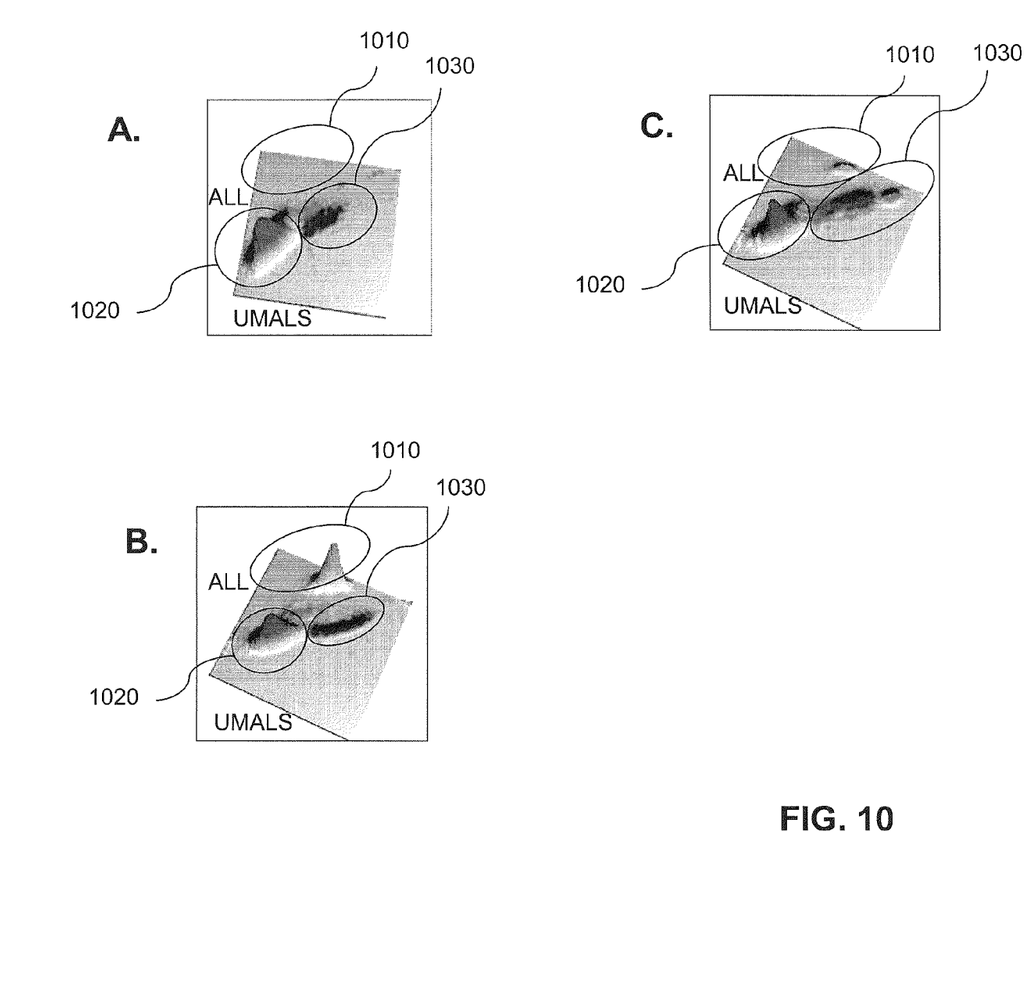
FIG. 10(A) shows a three-dimensional view of the event data from the analysis of a blood sample from a healthy individual. Hard-to-ghost cells 1010, mature red blood cells 1020, and reticulocytes 1030 are distinctly differentiated in the view.
FIG. 10(B) shows a three-dimensional view of the event data from the analysis of a blood sample from a patient diagnosed with sickle cell anemia. Hard-to-ghost cells 1010, mature red blood cells 1020, and reticulocytes 1030 are distinctly differentiated in the view.
FIG. 10(C) shows a three-dimensional view of the event data from the analysis of a blood sample from a patient diagnosed with Thalassemia. Hard-to-ghost cells 1010, mature red blood cells 1020, and reticulocytes 1030 are distinctly differentiated in the view.
Figure 11:
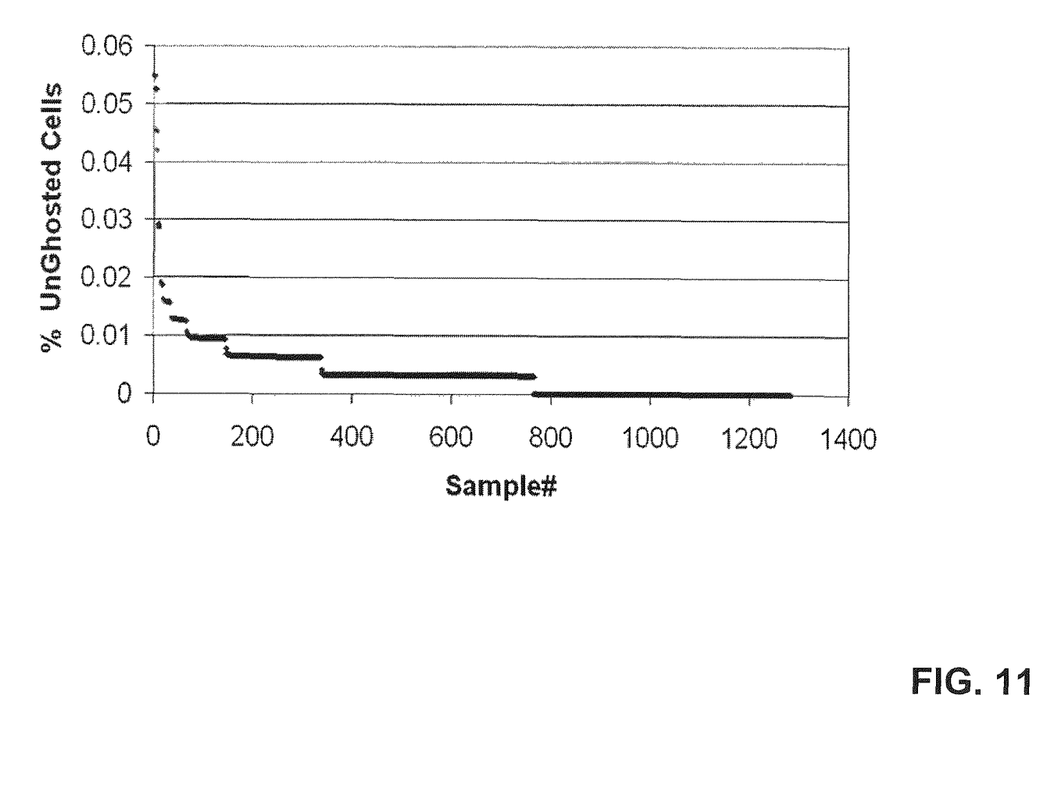
FIG. 11 illustrate an average % of "hard-to-ghost" cells in blood samples drawn from healthy individuals.
Figure 12:
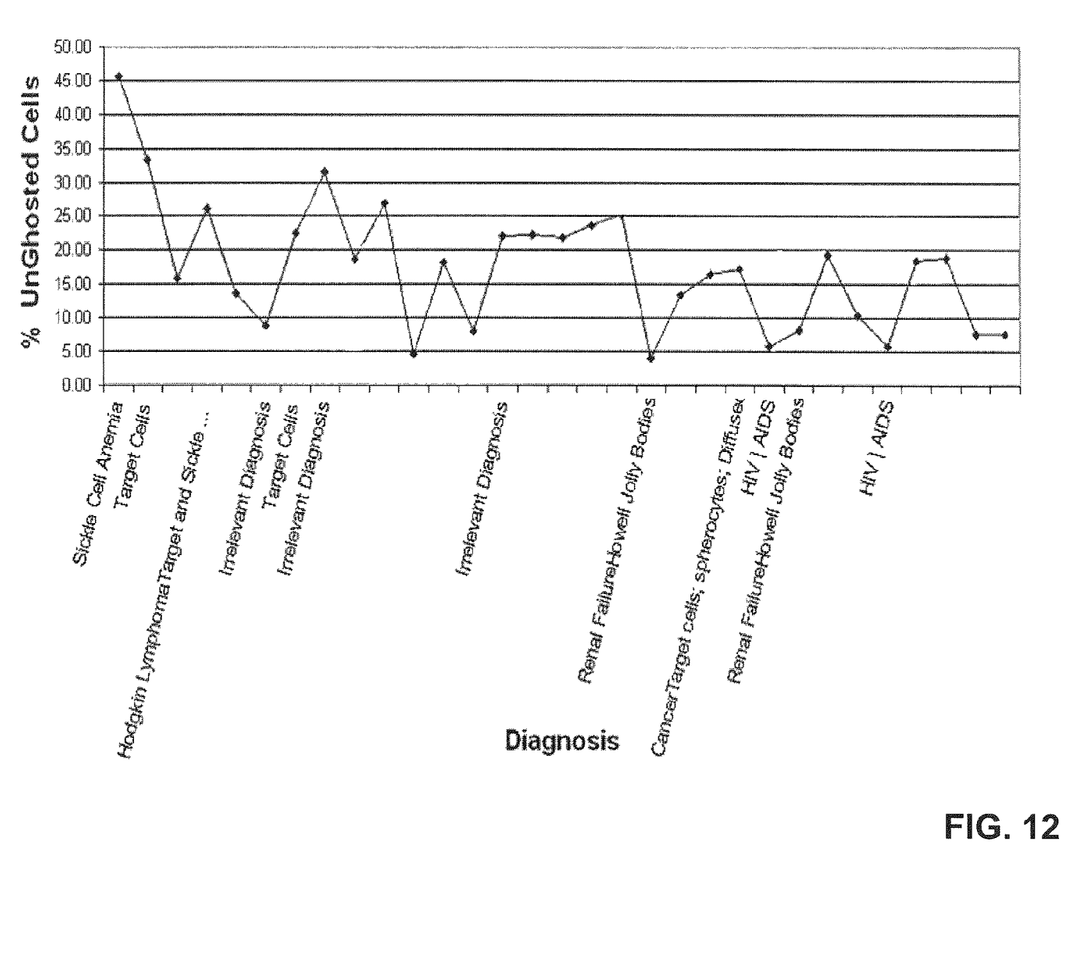
FIG. 12 illustrate an average % of "hard-to-ghost" cells in blood samples drawn from patients suffering from various diseases.

One aspect of the present invention is concerned with enumerating the hard-to-ghost cells in the blood sample. It has been unexpectedly discovered by the inventors of the present invention that there exists a correlation between the hard-to-ghost cell population in a blood sample and a blood pathology. Specifically, it has been found that the number of hard-to-ghost cells is increased in analyzed blood samples collected from patients suffering from various diseases, examples of which include, but are not limited to, diseases such as hemoglobinopathies, (e.g., sickle cell anemia and Thalassemia), hematological malignancies (e.g., leukemias and lymphomas), clotting and bleeding disorders, as well as HIV/AIDS, malignant tumors, and autoimmune disorders. In addition, further information can be obtained about these diseases when comparing the position of the hard-to-ghost cells in the scattergram to normal samples. Returning to FIG. 8, following the detection, hard-to-ghost cells can be enumerated, as in step 813. Counting or enumerating of cells is a well-established technique for well-defined cell populations, such as the presently defined hard-to-ghost cells. In one embodiment the hard-to-ghost fraction is reported as the ratio of hard-to-ghost cells to the entire red blood cell population. In another embodiment hard-to-ghost cells can be reported as a percentage or absolute number. Said value can be used as a research use only (RUO) parameter, or can be developed into an in vitro diagnostic (IVD) parameter. FIGS. 10 (A-C) illustrate the difference in size of hard-to-ghost cell populations 1010 in blood samples derived from a healthy individuals (FIG. 10(A)) and from patients suffering from sickle cell anemia (FIG. 10(B)) and Thalassemia (FIG. 10(C)). As illustrated by the FIGS. 10(A) and 11, the % hard-to-ghost cells of a total RBC population is negligible, i.e., less than about 0.01% in blood samples donated by healthy individuals. It has also been determined that blood samples from patients suffering from a number of certain pathologies contain an increased population of hard-to-ghost cells (illustrated in FIG. 12). Such pathologies include renal failure, liver cancer, HIV, sickle cell anemia, and thalassemia. The % hard-to-ghost cells of a total RBC population in a blood sample of a patient with a certain diagnosed disease state is increased at least 10-fold from the hard-to-ghost cell population size of a healthy individual. In some blood samples, the hard-to-ghost cell population of a patient suffering from a disease or disorder is at least 100-fold greater than that of a healthy individual. The discovery of this trend by the inventors of the present invention can be useful in determining existence of abnormal population of hard-to-ghost cells, which may further be related to a presence of certain pathologies.

Alternate methods can be employed to enumerate hard-to-ghost cells. More particularly, one skilled in the art can analyze a blood sample by ghosting the sample and measuring cell by cell hemoglobin of the blood cell sample using light scatter measurement as known to those skilled in the art. Those cells which have greater than 30% of the original hemoglobin are considered hard-to-ghost cells. In other words, the hard-to-ghost cells will have greater light scatter than a ghosted cells in the scattergram. In this alternate method, one skilled in the art could also employ a fluorescent dye to differentiate the reticulocytes from the hard-to-ghost cells.

It will be understood by a skilled artisan that the environments in which this invention can be practiced, such as flow cytometers and hematology analyzers, can be programmed to report a numerical value for hard-to-ghost cell population. This numerical value can be correlated to a biochemical and/or a physiological state of an individual. For example, a threshold value can be set for % hard-to-ghost cell of total red blood cells in a blood sample that corresponds to the number of hard-to-ghost cells present in a healthy individual. When a number of hard-to-ghost cells in a blood sample derived from a patient exceeds such threshold value, a disease state can be suspected and the blood sample can be reported, warranting further diagnostic evaluation of the patient. A physician assessing the blood count result will determine the appropriate further testing based on patient's symptoms, general health status, disease or disorder, gender, and age. In one embodiment, a blood sample can be reported for further evaluation if % hard-to-ghost cell in a blood sample exceeds the threshold value by at least 10-fold. In another embodiment, a blood sample can be reported for further evaluation if % hard-to-ghost cell in a blood sample exceeds the threshold value by at least 100-fold.

System to Determine Blood Cell Information

Figure 9:
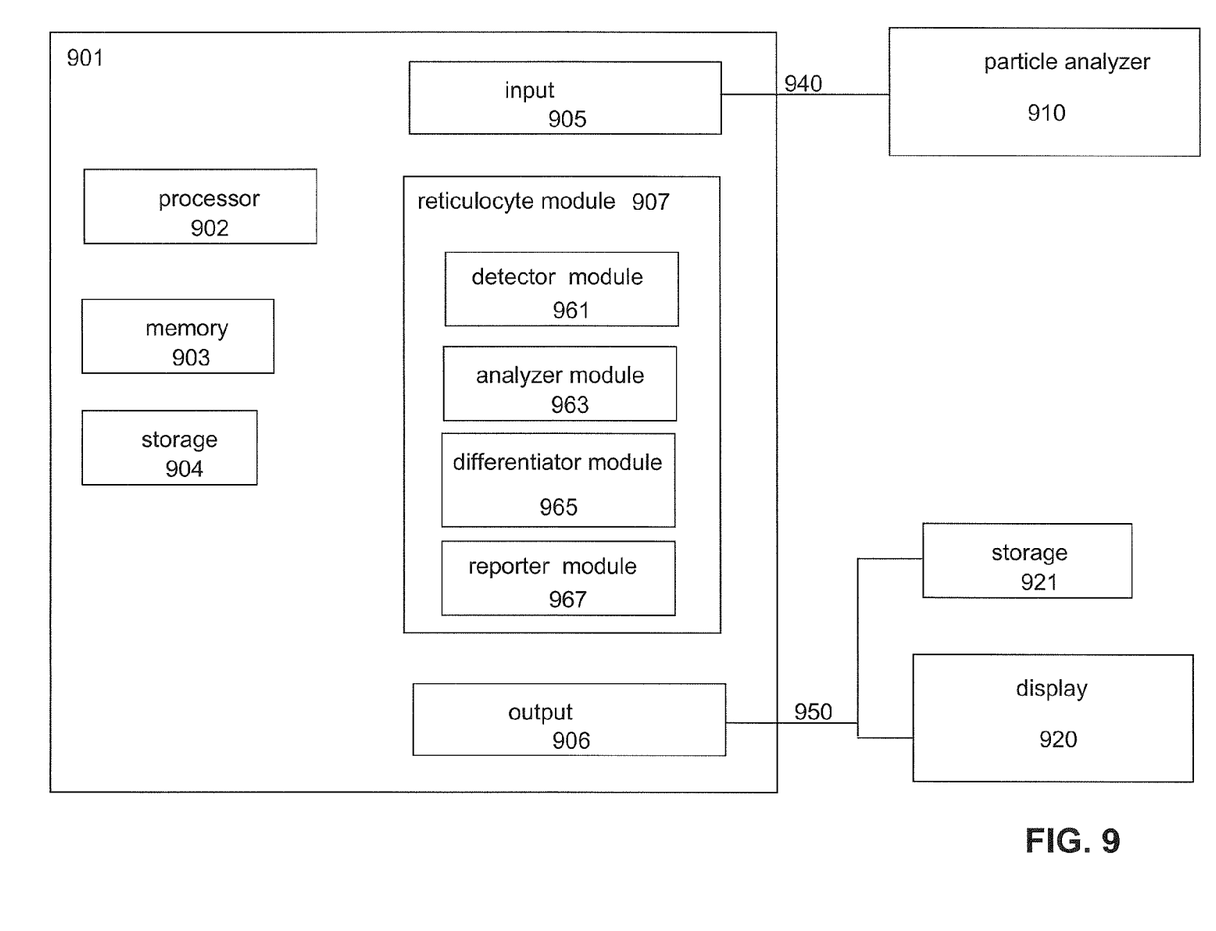
FIG. 9 is a system for evaluating immature reticulocytes according to an embodiment of the present invention.

FIG. 9 shows a system to analyze blood samples according to an embodiment of the present invention. A particle analyzer 910 is coupled using link 940 to a computer 901. Computer 901 is optionally coupled using link 950 to a display 920, and/or an external storage device 921. Computer 901 can include a processor 902, a memory 903, an internal storage 904, an input module 905, an output module 906, and a reticulocyte module 907. Reticulocyte module 907 can include a detector module 961, an analyzer module 963, a differentiator module 965, and a reporter module 967.

Particle analyzer 910 can include a hematology analyzer, flow cytometer, or similar device that is capable of interrogating a blood sample with the use of a beam of light. A blood sample is prepared an input to particle analyzer 910 for analysis. The event data generated by particle analyzer 910 is communicated to computer 901, over the link 940. Link 940 can be a device-internal connection such as peripheral component interconnect (PCI) bus, or a network connection. The events generated by the analysis of blood samples in particle analyzer 910 can be communicated to computer 901 in real-time or in batch-mode.

The event data, subsequent to any processing within computer 901, is then presented to a user on display 920, or stored in external storage device 921. For example, scatter plots generated by processing within computer 901 can be presented to the user using display 920. Processed event data can also be stored for later analysis and display. External storage device 921 can include a hard drive, or other type of portable storage.

Processor 902 can execute instructions that enable the processing of modules 905, 906 and 907. Internal memory 903 provides the temporary memory required for such processing, and internal storage 904 can provide for the temporary or intermediate storage of data and results associated with such processing. Internal storage 904 can also store control logic based on instructions and/or program code of modules including the component modules of reticulocyte module 907, in the forms including computer readable program code.

Input module 905 receives the event data generated by particle analyzer 910. Input module 905 can include any processing that is required to transform the input event data from particle analyzer 910, to a format understood by reticulocyte module 907. Output module 906 collects the event data processed by reticulocyte module 907, performs any conversion necessary, and outputs to either display 920 or storage 920, using link 950. Link 950 can be an device-internal connection such as PCI, or a network connection. Display 920 can be a display device that is customized for the viewing of particle analyzer data, a generic display, or any other means capable of outputting results of the particle analysis.

The detector module 961 can include the instructions for determining measurements or parameters of cell events as they pertain to side scatter including UMALS, forward scatter, axial light loss, and DC. Note that every embodiment of the present invention may not have access to all of the measurements above. There may be some configuration required on particle analyzer 910 to enable the collection of all of the above measurements.

Analyzer module 963 includes the instructions for identifying the reticulocyte population and/or a hard-to-ghost cell population, and isolating that population from other types of blood cells. In another embodiment, analyzer module 963 can include instructions to filter-out the cell events corresponding to hard-to-ghost cells, as explained above. In yet another embodiment, analyzer module 963 can include instructions for enumerating the hard-to-ghost cell population.

Differentiator module 965 can include instructions that cause the computer to determine the immature reticulocyte information of the sample being analyzed. For example, the reticulocyte event population identified using module 963, may now be investigated using both, the light scatter measurement as well as a second reticulocyte maturity measurement such as volume, to differentiate the mature from the immature reticulocytes.

Reporter module 967 includes the instruction enabling computer 901 to display scatter plots to display 920, and also to report useful quantifications of the reticulocytes in the blood sample. The reticulocyte fraction or the reticulocyte percentage are some quantifications that can be reported by reporter module 967. Reporter module 967 can also include instructions to report information about hard-to-ghost cell populations.

In this disclosure, methods were disclosed that can improve the accuracy of blood sample analysis through measures such as the reticulocyte fraction and hard-to-ghost cells. The disclosed methods yield substantial improvements over the current methods and can lead to significant improvements in the detection and treatment of a number of blood pathologies. Persons skilled in the art will understand that the techniques disclosed herein can be applicable for cell types other than erythrocytes as described here.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. An automated method of enumerating hard-to-ghost cells in a blood cell sample comprising: (a) mixing a blood cell sample with a nucleic acid stain to stain nucleic acid and a ghosting reagent to remove hemoglobin from red blood cells in the blood cell sample, thereby generating a ghosted blood cell sample, wherein the sample comprises hard to ghost cells containing residual hemoglobin; (b) passing the ghosted blood cell sample through a cytometric flow cell; (c) analyzing the ghosted blood cell sample in the cytometric flow cell using an Axial Light Loss measurement and a second optical measurement; (d) differentiating hard-to-ghost cells in the ghosted blood cell sample from other cells using the analysis by Axial Light Loss and the second optical measurement; and (e) enumerating the hard-to-ghost cells.

2. The method of claim 1, wherein mixing of the blood sample with the nucleic acid-staining dye and the ghosting reagent is performed separately.

3. The method of claim 1, wherein the stain is fluorescent or non-fluorescent.

4. The method of claim 1, wherein the second optical measurement comprises fluorescence or light scatter.

5. The method of claim 1, further comprising determining an existence of an abnormal population of hard-to-ghost cells by comparing the number of hard-to-ghost cells in the blood cell sample to a threshold value and reporting the number of hard-to-ghost cells that exceeds the threshold value.

6. An automated method of enumerating hard-to-ghost cells in a blood cell sample comprising: (a) mixing a blood cell sample with a nucleic acid-staining fluorescent dye to stain the blood cells containing nucleic acid and a ghosting reagent to remove hemoglobin from red blood cells in the blood cell sample, thereby generating a ghosted blood cell sample wherein the sample comprises hard to ghost cells containing residual hemoglobin; (b) passing the ghosted blood cell sample through a cytometric flow cell; (c) analyzing the ghosted blood cell sample in the cytometric flow cell by using Axial Light Loss and fluorescence measurements; (d) differentiating hard-to-ghost cells from the fluorescently stained cells and ghosted cells using the analysis by the fluorescence and Axial Light Loss measurements; and (e) enumerating the hard-to-ghost cells.

7. The method of claim 6, wherein mixing of the blood sample with the nucleic acid-staining fluorescent dye and the ghosting reagent is performed separately.

8. The method of claim 6, further comprising determining an existence of an abnormal population of hard-to-ghost cells by comparing the number of hard-to-ghost cells in the blood cell sample to a threshold value and reporting the number of hard-to-ghost cells that exceeds the threshold value.

9. The method of claim 8, wherein the abnormal population of hard-to-ghost cells is associated with hemoglobinopathy.

10. The method of claim 9, wherein hemoglobinopathy comprises sickle cell anemia or thalassemia.

11. An automated method of enumerating hard-to-ghost cells in a blood cell sample comprising: (a) mixing a blood cell sample with a ghosting reagent to remove hemoglobin from red blood cells in the blood cell sample, thereby generating a ghosted blood cell sample wherein the sample comprises hard-to-ghost cells containing residual hemoglobin; (b) passing the ghosted blood cell sample through a cytometric flow cell; (c) analyzing the ghosted blood cell sample in the cytometric flow cell using an Axial Light Loss measurement; (d) differentiating hard-to-ghost cells in the ghosted blood cell sample from other cells using the analysis by Axial Light Loss; and (e) enumerating the hard-to-ghost cells.

* * * * *